United States Patent
Tomie et al.

(10) Patent No.: US 7,041,808 B2
(45) Date of Patent: May 9, 2006

(54) ANTIMICROBIAL PROTEINS, GENES ENCODING THE PROTEINS AND METHOD OF USING THE SAME

(75) Inventors: Tetsuya Tomie, Saitama (JP); Michito Tagawa, Saitama (JP); Minoru Yamakawa, Ibaraki (JP); Jun Ishibashi, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 10/492,607

(22) PCT Filed: Oct. 15, 2002

(86) PCT No.: PCT/JP02/10651

§ 371 (c)(1),
(2), (4) Date: Nov. 26, 2004

(87) PCT Pub. No.: WO03/033532

PCT Pub. Date: Apr. 24, 2003

(65) Prior Publication Data

US 2005/0069977 A1  Mar. 31, 2005

(30) Foreign Application Priority Data

Oct. 15, 2001  (JP)  .............................. 2001-317255

(51) Int. Cl.
*C07K 14/435* (2006.01)
*A61K 38/17* (2006.01)
*A01N 63/02* (2006.01)
*C12P 21/02* (2006.01)

(52) U.S. Cl. ........................ 530/858; 530/324; 514/12; 504/117; 435/69.1; 435/70.1

(58) Field of Classification Search ................ 530/858, 530/324; 514/12; 504/117; 435/69.1, 70.1
See application file for complete search history.

(56) References Cited

FOREIGN PATENT DOCUMENTS

WO  WO 9507353 A2 * 3/1995

OTHER PUBLICATIONS

Result 8 from Geneseq database search, alignment with SEQ ID No.: 4 of Sim et al. (WO 95/07353), pp. 42-46, Plasmodium falciparum sialic acid binding protein.*

Jun Yang et al., Isolation, cDNA cloning and gene expression of an antibacterial protein from larvae of the coconut rhinoceros beetle, *Oryctes rhinoceros*. European Journal of Biochemistry 1998, vol. 255, No. 3, pp. 734-738.

(Continued)

*Primary Examiner*—Robert A. Wax
*Assistant Examiner*—Rosanne Kosson
(74) *Attorney, Agent, or Firm*—Thompson Coburn LLP (57) ABSTRACT

It is intended to provide thermotolerant and antimicrobial proteins having a broad antibacterial spectrum and being useful in the agricultural, medical and industrial field; and plants resistant to pathogenic microorganisms. Namely, DNAs comprising the base sequences represented by SEQ ID NOS: 1 to 5 respectively; antimicrobial proteins encoded by these DNAs; and fungicides, antibacterial agents and antibacterial/antifungal agents for industrial use comprising the antimicrobial proteins as the active ingredient.

3 Claims, 2 Drawing Sheets

OTHER PUBLICATIONS

Seiichi Furukawa et al., Partial nucleotide sequence of a cDNA encoding 18S ribosomal RNA from the coconut rhinoceros beetle, *Oryctes rhinoceros* Linnaeus. Applied Entomology and Zoology 1998, vol. 33, No. 1, pp. 175-178.

Jun Ishibashi et al., Purification, cDNA cloning and modification of a defensin from the coconut rhinoceros beetle, *Oryctes rhinoceros*. European Journal of Biochemistry 1999, vol. 266, No. 2, pp. 616-623.

Tetsuya Tomie et al. Scarabaecin, a novel cysteine-containing antifungal peptide from the rhinoceros beetle, *Oryctes rhinoceros*. Biochemical and Biophysical Research Communications 2003, vol. 307, pp. 261-266.

Hikaru Hemmi et al. Structural Basis for New Pattern of Conserved Amino Acid Residues Related to Chitin-binding in the Antifungal Peptide from the Coconut Rhinoceros Beetle *Oryctes rhinoceros*. The Journal of Biological Chemistry, vol. 278, No. 25, pp. 22820-22827.

Patent Cooperation Treaty; International Search Report; Jan. 14, 2003.

European Patent Office; Supplementary European Search Report; Nov. 2, 2004.

\* cited by examiner

ANTIMICROBIAL PROTEINS, GENES ENCODING THE PROTEINS AND METHOD OF USING THE SAME

TECHNICAL FIELD

The present invention relates to novel proteins having an antimicrobial activity, genes encoding the proteins, and a method of utilizing the proteins and genes.

BACKGROUND ART

As antimicrobial proteins derived from insects, nearly 150 proteins have been found in many kinds of insects. Among these proteins, those reported to be active against filamentous fungi include drosomycin from Diptera insects (J. Biol. Chem., 1994; 269 (52): 33159–33163), heliomicin from *Lepidoptera* insects (J. Biol. Chem. 1999; 274 (14): 9320–9326), thanatin from *Hemiptera* insects (Proc. Natl. Acad. Sci. USA 1996; 93: 9320–9326) etc.

As antimicrobial peptides from the coconut rhinoceros beetle (*Oryctes rhinoceros*) i.e. a *Coleoptera* insect, on one hand, there are reported tryphacin (JP-A 8-283291), oryctin (JP-A8-283292), rhinocerasin (JP-A8-283294) and defensin (Eur. J. Biochem. 1999; 266: 616–623), but antimicrobial proteins active against filamentous fungi are still not known.

In recent years, it is attempted to confer disease resistance by introducing antimicrobial protein genes obtained from insects into plants. Tobacco plants transformed with sarcotoxin IA obtained from *SARCOPHAGA PEREGRINA* (Mol. Plant. Microbe. Interact. 2000; 13(8) 860–868), rice plants transformed with cecropin B obtained from silkworms (FEBS Letters 2000; 484: 7–11) etc. are reported but still not practically used. This is probably because the gene introduced into the plant was not obtained as a gene of a protein active against plant-pathogenic filamentous fungi exerting significant damage to the plant. Accordingly, it is desired that an antimicrobial protein which is more active against filamentous fungi than the conventional antimicrobial proteins, and its gene, are identified and used.

As the industrial antimicrobial/antifungal agents, an organic nitrogenous compound, an organic nitrogenous sulfurous compound, an organohalogen compound, a nitrogen-containing aliphatic polymer and a heavy metal-coordinated compound have been used. However, these compounds contain chemicals which are stimulative and problematic in the labor safety law, chemicals used in a large amount to cause a problem from the viewpoint of environmental protection, chemicals releasing formalin or halogens to cause worry about their influence on the human body and about environmental pollution, and chemicals by which environmental pollution with heavy metals is worried about, and it cannot be said that the industrial antimicrobial/antifungal agents are composed exclusively of preferable chemicals.

In medical fields, on one hand, multiple drug resistance microorganisms which are resistant to, for example, antibiotics such as methicillin and vancomycin come to be problematic, and there is demand for useful chemicals effective against these multiple drug resistance microorganisms.

DISCLOSURE OF INVENTION

In the present invention, a novel antimicrobial protein which can suppress growth of various plant-pathogenic microorganism at a relatively low concentration was screened and determined, a gene encoding the protein was cloned, its nucleotide sequence was specified, and the gene of the present invention was introduced into suitable hosts (microorganisms, animals or plants) to create transformants, thus utilizing the gene of the present invention. Another object of the present invention is to provide agricultural and horticultural fungicides and pharmaceutical or industrial antimicrobial/antifungal agents, which comprise the antimicrobial protein of the present invention.

MEANS TO SOLVE THE PROBLEM

First, the present inventors established an assay system for assaying an antimicrobial activity in vitro against *Rhizoctonia solani*. Then, a protein component was extracted from hemolymph of Coconut rhinoceros beetle larvae and subjected to a combination of various kinds of column chromatography, and each fraction was subjected to the assay system, whereby an antimicrobial protein fraction was identified and an antimicrobial protein was successfully isolated and purified.

Further, the present inventors determined a partial amino acid sequence of the purified protein, isolated a full-length cDNA encoding the protein by RT-PCR using oligonucleotides synthesized as primers from the determined amino acid sequence, and determined the whole nucleotide sequence. As described above, the present inventors succeeded in isolation of a novel antimicrobial protein derived from the coconut rhinoceros beetle and in cloning a DNA encoding the same, and determined an amino acid sequence of the protein and a nucleotide sequence of the DNA, thus arriving at the present invention.

(DNA)

The DNAs of the present invention are DNAs encoding respectively five proteins having an antimicrobial activity described later.

The DNA can be isolated and identified from DNA and RNA extracted from Coconut rhinoceros beetle larvae, but may be a DNA prepared on the basis of the sequence disclosed in this specification by cloning using general genetic engineering techniques such as hybridization or by chemical synthetic techniques such as a phoshoamidite method. The DNA may be in a form which includes, but is not limited to, cDNA, genomic DNA and chemically synthesized DNA. The DNA of the present invention may be a single strand or may bind to DNA or RNA having a sequence complementary thereto to form a double or triple strand. The DNA may be labeled with an enzyme such as horse radish peroxidase (HRPO), a radioisotope, a fluorescent substance, a chemoluminescent substance etc.

Given the nucleotide sequence of the DNA of the present invention, the sequence of RNA derived therefrom, and the sequence of its complementary DNA or RNA can be principally determined, and thus the present invention should also be construed to provide an RNA corresponding to the DNA of the present invention, or a DNA and RNA having a sequence complementary to the DNA of the present invention.

Further, the DNA of the present invention also encompasses DNAs hybridizing under stringent conditions with any one of DNAs consisting of the nucleotide sequences represented by SEQ ID NOS: 1 to 5.

Variations in nucleotide sequences of the DNAs of the present invention are allowable in such a range that the DNAs hybridize under stringent conditions with the DNAs consisting of the nucleotide sequences represented by SEQ ID NOS: 1 to 5 and the proteins encoded by the DNAs maintain an antimicrobial activity. For example, DNA sequences altered partially by the presence of a plurality of codons which owing to codon degeneracy, encode the same amino acid sequence or by various artificial treatments such as site-specific mutagenesis and random mutation by treatment with a mutagen, or by mutating, deleting and ligating their DNA fragment by cleavage with restriction enzymes can, regardless of their difference from the DNA sequences represented by SEQ ID NOS: 1 to 5, fall under the scope of the resent invention insofar as the DNA mutants hybridize under stringent conditions with any one of the DNAs represented by SEQ ID NOS: 1 to 5 and simultaneously encode proteins having an antimicrobial activity.

The DNAs may be mutated in such a degree that they have 70% or more, preferably 80% or more, more preferably 90% or more, homology to any one of the DNA sequences represented by SEQ ID NO: 1 to 5. The hybridization of the DNAs with any one of the nucleic acids represented by SEQ ID NOS: 1 to 5 may be in such a degree that after hybridization under usual conditions, for example, after the DNAs labeled with a probe by using a DIG DNA Labeling kit (Cat No. 1175033 manufactured by Boehringer Mannheim) are subjected to Southern hybridization in a DIG Easy Hyb solution at 32° C. (Cat No. 1603558 manufactured by Boehringer Mannheim) and then their bound membrane is washed with a 0.5×SSC solution (containing 0.1% (w/v) SDS) (1 ×SSC: 0.15 M NaCl, 0.015 M sodium citrate) at room temperature, the DNAs remain hybridized.

The DNA of the present invention is introduced into a suitable vector to form a recombinant vector preferably an expression vector which can be preferably used in producing its coding protein having an antimicrobial activity by genetic recombination techniques. The recombinant vector may be in any forms such as cyclic or linear forms. The recombinant vector may also have other nucleotide sequences if necessary in addition to the DNA of the present invention. The other nucleotide sequences include nucleotide sequences such as an enhancer sequence, a promoter sequence, a ribosome-binding sequence, a nucleotide sequence used for the purpose of amplification of copy number, a nucleotide sequence encoding a signal peptide, a nucleotide sequence encoding another polypeptide, a poly A-added sequence, a splicing sequence, an origin of replication, and a gene serving as a selective marker.

In genetic recombination, a translation initiation codon or a translation termination codon is added via a suitable synthetic DNA adaptor to the DNA of the present invention, or suitable restriction enzyme cleavage sites are newly generated or eliminated in the nucleotide sequence. These procedures can be carried out usually by those skilled art in processing the recombinant DNA arbitrarily and easily on the basis of the DNA of the present invention.

As the vector harboring the DNA of the present invention, a suitable vector compatible with a host used may be selected and used, and not only plasmids but also viruses such as bacteriophage, Baculovirus, retrovirus, vaccinia virus etc. can be used without particular limitation.

Oligonucleotides consisting of nucleotide sequences hybridizing with any one of the DNAs represented by SEQ ID NOS: 1 to 5 in the present invention, for example, oligonucleotides represented by SEQ ID NOS: 12 to 18, can serve as primers in RT-PCR using as a template a cDNA of fat body of Coconut rhinoceros beetle larvae. By this PCR method, a full-length cDNA clone encoding the antimicrobial protein of the present invention can be easily isolated to provide a method of isolating the gene of the present invention.

(Protein Having an Antimicrobial Activity)

The protein of the present invention is a protein having an antimicrobial activity, comprising an amino acid sequence represented by one of SEQ ID NOS: 6 to 10. The antimicrobial activity referred to herein means an activity of suppressing or killing a wide variety of microorganisms ranging from various filamentous fungi to various bacteria. The antimicrobial activity refers in particular to an activity of suppressing or killing plant-pathogenic filamentous fungi and bacteria giving severe damage in agriculture, filamentous fungi and bacteria causing severe infectious disease in medicine, and filamentous fungi and bacteria giving severe damage in industry.

Although the protein of the present invention can be prepared from hemolymph of Coconut rhinoceros beetle larvae, particularly 3-week-old larvae, having an antimicrobial effect on plant-pathogenic microorganism, its origin, process etc. are not particularly limited insofar as the resulting protein has the features described in this specification. That is, the protein of the present invention may be a protein derived from a natural source, a protein expressed from the recombinant DNA by genetic engineering techniques, or a chemically synthesized protein.

The protein represented by SEQ ID NO: 6 is a protein consisting of 66 amino acid residues in total. It is estimated that this protein undergoes processing to cleave its N-terminal and/or C-terminal to generate a protein (SP4080) consisting of 36 amino acid residues in total represented by SEQ ID NO:7, a protein (SP4266) consisting of 38 amino acid residues in total represented by SEQ ID NO:8, a protein (SP4337) consisting of 38 amino acid residues in total represented by SEQ ID NO:9 and a protein (SP4523) consisting of 40 amino acid residues in total represented by SEQ ID NO:10, respectively. In this manner, the amino acid sequences represented by SEQ ID NOS: 7 to 10 correspond respectively to partial amino acid sequences of the amino acid sequence represented by SEQ ID NO:6.

As a result of investigation of homology with a known protein data base, a known amino acid sequence having homology of more than 50% with the amino acid sequences of the proteins having an antimicrobial activity according to the present invention could not be confirmed. Accordingly, the protein having an antimicrobial activity according to the present invention is considered to be a protein consisting of a novel characteristic amino acid sequence.

The proteins of SEQ ID NOS: 6 to 10 are proteins which even after heat treatment at 100° C. for 10 minutes, have an antimicrobial activity on plant-pathogenic microorganism.

The protein of the present invention exhibits an activity of suppressing or killing a wide variety of microorganisms ranging from filamentous fungi to bacteria, for example plant-pathogenic microorganism such as *Rhizoctonia solani*, *Pyricularia oryzae*, *Septoria tritici*, *Rhizoctonia solani* Kuhn and *Phytophthora* infestance, and sanitary pathogenic microorganism such as *Staphylococcus aureus* and *Escherichia coli*. In particular, the protein of the present invention exhibits a significant antimicrobial activity on *Rhizoctonia solani*, *Rhizoctonia solani* Kuhn, *Staphylococcus aureus* and *Escherichia coli*.

Polypeptides or proteins consisting of those amino acid sequences represented by SEQ ID NOS: 6 to 10 wherein one or more amino acids are substituted, deleted and/or added fall under the scope of the present invention insofar as they possess the antimicrobial activity described above.

Amino acid residue serving as elements of the protein are different from one another in respect of hydrophobicity, charging, size etc., but the relationship between amino acids highly preserved in such a meaning as not to substantially give influence on the three-dimensional structure (also called stereostructure) of the entire protein. For example, the following amino acid residues can be exchanged with each other: glycine (Gly) and proline (Pro), Gly and alanine (Ala) or valine (Val), leucine (Leu) and isoleucine (Ile), glutamic acid (Glu) and glutamine (Gln), aspartic acid (Asp) and asparagine (Asn), cysteine (Cys) and threonine (Thr), Thr and serine (Ser) or Ala, lysine (Lys) and arginine (Arg), etc. Many mutations where even if preservation in the meaning described above is lacking, the essential function of the protein is maintained (in the present invention, the antimicrobial activity is maintained) are known by those skilled in the art. Further, it is often recognized that the same kind of protein preserved among different biological species maintains its essential function even if some amino acids are concentrically or dispersively deleted or inserted.

Accordingly, it can be said that mutant proteins with substitutions, insertions, deletions etc., derived from the amino acid sequences represented by SEQ ID NOS: 6 to 10, fall under the scope of the present invention insofar as the mutant proteins are protein having the antimicrobial activity as the essential function of the present invention.

Such modifications to amino acids, such as mutations occurring due to genetic polymorphism etc., are not only recognized in the natural world but can also be artificially carried out by methods known by those skilled in the art, for example by utilizing mutagenesis using a mutagen such as NTG and site-directed mutagenesis using various recombinant gene techniques. The site and number of mutated amino acids are not particularly limited insofar as the mutant protein maintains the antimicrobial activity, but usually the number of mutated amino acids is not greater than 20, preferably not greater than 10.

(Transformed Plant)

The transformed plant of the present invention is a plant (or an offspring thereof) rendered resistant to plant-pathogenic microorganism by expressing the protein having an antimicrobial activity according to the present invention, which is regenerated on the basis of host plant cells transformed with the gene of the present invention located under the control of a suitable promoter capable of functioning in plant cells, or with the gene of the present invention integrated in a suitable vector.

The transformed plant of the present invention can express, in the plant body, the protein having an antimicrobial activity according to the present invention.

The transformed plant of the present invention include all plant species including, for example, monocotyledonous plants such as *Gramineae*, *Palmae*, *Liliaceae*, *Orchidaceae*, *Araceae*, etc.

The *Gramineae* plant includes rice, wheat, barley, rye, turf, reed, sugarcane, corn, foxtail, barnyard grass, etc.

The *Liliaceae* plant includes long green onion, lily, tulip, etc.

The dicotyledonous plant includes *Fagaceae*, *Cactaceae*, *Theaceae*, *Malvaceae*, *Cucurbitaceae*, *Cruciferae*, *Rosaceae*, *Leguminosae*, *Euphorbiaceae*, *Vitaceae*, *Rutaceae*, *Umbelliferae*, *Solanaceae*, *Labiatae*, *Compositae*, *Primulaceae*, etc.

The *Theaceae* plant includes tea etc.

The *Malvaceae* plant includes cotton etc.

The *Cucurbitaceae* plant includes cucumber, melon, pumpkin etc.

The *Cruciferae* plant includes rape, *Arabidopsis thaliana*, Japanese white radish, Japanese horseradish, cabbage etc.

The *Rosaceae* plant includes Japanese apricot, peach, apple, pear, rose etc.

The *Leguminosae* plant includes soybean, adzuki bean, pea, broad bean, peanut etc.

The *Solanaceae* plant includes tobacco, eggplant, potato, tomato etc.

The *Compositae* plant includes *chrysanthemum*, garland *chrysanthemum*, sunflower, lettuce etc.

The *Primulaceae* includes primrose, *cyclamen* etc.

Further, plants belonging to gymnosperms such as *Taxodiales*, *Pinales*, *Chamaecyparis*, etc. are also contained in the transformed plant of the present invention.

(Antimicrobial Agent, Fungicide and Industrial Antimicrobial/Antifungal Agent)

The antimicrobial agent, fungicide or industrial antimicrobial/antifungal agent according to the present invention is prepared by using the protein having an antimicrobial activity alone as the active ingredient or by combining it with a suitable excipient etc. Because of the broad antimicrobial spectrum of the protein having an antimicrobial activity as the active ingredient, the protein is preferably used as an agricultural and horticultural fungicide, an antimicrobial agent for pharmaceutical preparations and an industrial antimicrobial/antifungal agent.

In any cases, the antimicrobial protein of the present invention can be used alone, or may be used in combination if necessary with other known agrochemicals, pharmaceutical preparations, industrial antimicrobial/antifungal components, insecticidal components etc. Further, the protein having an antimicrobial activity used as the active ingredient in the present invention may be composed of a single protein or a mixture of several kinds of proteins.

The plant diseases to which the agricultural and horticultural fungicides of the present invention is applied include a wide variety of diseases including *Pyricularia oryzae*, *Cochliobolus miyabeanus*, *Rhizoctonia solani*, *Erysiphe graminis* f. SP. *hordei*, f. SP. *tritici*, *Pyrenophora graminea*, *Pyrenophora teres*, *Gibberella zeae*, *Puccinia striiformis*, *P. graminis*, *P. recondita*, *P. hordei*, *Typhula* SP., *Micronectriella nivais*, *Ustilago tritici*, *U. nuda*, *Pseudocercosporella herpotrichoides*, *Rhynchosporium secalis*, *Septoria tritici*, *Leptosphaeria nodorum*, *Diaporthe citri*, *Elsinoe fawcetti*, *Penicillium digitatum*, *P. italicum*, *Sclerotinia mali*, *Valsa mali*, *Podosphaera leucotricha*, *Alternaria mali*, *Venturia inaequalis*, *Venturia nashicola*, *Alternaria Kikuchiana*, *Gymnosporangium haraeanum*, *Sclerotinia cinerea*, *Cladosporium carpophilum*, *Phomopsis*, sp., *Plasmopara viticola*, *Elsinoe ampelina*, *Glomerella cingulata*, *Uncinula necator*, *Phakopsora ampelopsidis*, *Gloeosporium kaki*, *Cercospora kaki*, *Mycosphaerella nawae*, *Pseudoperenospora cubensis*, *Colletotrichum lagenarium*, *Sphaerotheca fuliginea*, *Mycosphaerella melonis*, *Phytophthora infestans*, *Fusarium oxysporum*, *Alternaria solani*, *Cladosporium fulvam*, *Phomopsis vexans*, *Erysiphe cichoracoarum*, *Alternaria japonica*, *Cerocosporella brassicae*, *Puccinia allii*, *Cer-* cospora kikuchii, Elsinoe glycines, Diaporthe phaseololum, Colletotrichum lindemuthianum, Mycosphaerella personatum, Cercospora arachidicola, Erysiphe pisi, Alternaria solani, Sphaerotheca humuli, Exobasidium reticulatum, Elsinoe leucospila, Alternaria longipes, Erysiphe cichoracearum, Colletotrichum tabacum, Cercospora beticola, Diplocarpon rosae, Sphaerotheca pannosa, Septoria chrysanthemiindici, Puccinia horiana, Phizoctonia solani, Pythium spp., Sclerotinia homoeocarpa, Typhula spp, Fusarium nivale, Sclerotinia borealis, Helminthosporium sorokinianum, H. erythrospilum, Pythium periplocum, P. graminicola, P. vanterpoolii, Rhizoctonia solani, Borytis cinerea, Sclerotinia sclerotiorum etc. Accordingly, the protein having an antimicrobial activity according to the present invention can be used as an active ingredient in plant disease-controlling agents infields, paddy fields, lawn grounds, orchards, pastures, greenhouses, and other non-arable lands.

The antimicrobial agent for pharmaceutical preparations according to the present invention is useful in exhibiting an antimicrobial effect on pathogenic microorganism such as *Staphylococcus aureus, Escherichia coli*, microorganisms of the genus *Aspergillus*, microorganisms of the genus *Candida*, microorganisms of the genus *Mucor*, microorganisms of the genus *Absidia*, microorganisms of the genus *Cryptococcus*, microorganisms of the genus *Blastomyces*, microorganisms of the genus *Paracoccidioides*, microorganisms of the genus *Coccidioides*, microorganisms of the genus *Sporothrix*, microorganisms of the genus *Phialophora*, microorganisms of the genus *Histoplasma*, microorganisms of the genus *Trichophyton*, microorganisms of the genus *Microsporum*, microorganisms of the genus *Epidermophyton*, etc.

The protein having an antimicrobial activity used as the active ingredient in the industrial antimicrobial/antifungal agent of the present invention is blended and mixed with a suitable excipient and adjuvant, for example a binder, a stabilizer etc. to prepare a pharmaceutical preparation in a suitable form in a usual manner, such as a liquid, a hydrate, an emulsion, sol (flowable agent), etc.

The industrial antimicrobial/antifungal agent containing the protein having an antimicrobial activity as the active ingredient according to the present invention can be used in suppression of the growth of microorganisms and fungi in emulsion products such as aqueous paints, adhesive materials, latex, acryl etc., slurry products such as starch, pigments, calcium carbonate etc., and joint cement; preservation of wood such as building materials (construction materials, civil engineering building materials etc.); sterilization and prevention of slime formation in production facilities in factories, cooling towers in building air conditioning, and pulp- and paper-making factories, etc.; antimicrobial/antifungal treatment by spraying or dipping of fibers, fabrics and hides; protection from the attack of microorganisms and fungi occurring during exposure of a paint coating, particularly a paint coating of an exterior paint, to wind and rain; antimicrobial/antifungal treatment of interior/exterior materials (for housing, medical facilities), building materials (construction materials, civil engineering materials etc.), home appliances, domestic sundries, sporting goods etc. made of resin such as vinyl chloride, polyurethane, polyethylene, polypropylene, silicone, modified silicone, nylon, epoxy resin etc.; protection from accumulation of slime on devices for producing sugar cane and beet sugar; prevention of accumulation and sedimentation of microorganisms in an air washer and scrubber system and an industrial freshwater-feeding system; maintenance of sanitary environments in food factories etc.; deodorization and sterilization at the time of washing production facilities and in sewage disposal plants etc.; prevention of growth of microorganisms and fungi in paper-coating materials and coating processing; prevention of contamination of cosmetics and toiletries with microorganisms; prevention of microbial growth in a pool, cooling water etc.; prevention of microbial contamination of agricultural blends, an electrodeposition system, and diagnostic and chemical products, medical instruments etc.; and prevention of accumulation of microorganisms in photographic treatment.

The industrial antimicrobial/antifungal agent of the present invention formed into a pharmaceutical preparation can be used as it is, or used according to a wide variety of conventional methods of using industrial antimicrobial/antifungal agents, which include, but are not limited to, a method that involves diluting it with water or a suitable organic solvent and mixing the dilution with various industrial materials or products, a method of applying or spraying it onto the surfaces of various industrial materials or products, and a method that involves dipping various industrial materials or products in a dilution of the industrial antimicrobial/antifungal agent of the present invention, etc.

The fungicide, antimicrobial agent and industrial antimicrobial/antifungal agent of the present invention described above may be in the form of preparations prepared by mixing the protein with a solution, a suspension, an emulsion etc., for example in the form of tablets, pills, powder, granules, liquids, hydrates, emulsions, injections, poultices, suppositories, aerosol, sol (flowable agent) etc.

BEST MODE FOR CARRYING OUT THE INVENTION (DNA)

The DNA of the present invention can be cloned on the basis of a DNA or RNA extracted from Coconut rhinoceros beetle larvae, particularly 3-week-old larvae, according to the Examples in the present invention, and by using fundamental techniques of genetic engineering such as hybridization and PCR utilizing the nucleotide sequence disclosed in the present invention or a part thereof, a gene encoding a protein having a similar antimicrobial activity can also be isolated from other biological species. Further, a part or the whole of the DNA can be chemically synthesized by using a DNA synthesizer.

The hybridization conditions for screening a homologous gene derived from a creature other than Coconut rhinoceros beetle are not particularly limited, but generally, stringent conditions are preferable, and such conditions are for example hybridization conditions in 6×SSC, 5×Denhardt'S, 0.1% SDS, at 25 to 68° C. It is well-known by those skilled in the art that a DNA containing a nucleotide sequence having homology higher than a certain level can be cloned by suitably determining hybridization conditions such as formamide concentration, salt concentration and temperature.

The homologous gene cloned by using the hybridization described above is preferably the one having at least 70%, preferably at least 80%, more preferably at least 90% homology to the nucleotide sequences represented by SEQ ID NOS: 1 to 5.

Oligonucleotides having a nucleotide sequence represented by any one of SEQ ID NOS: 12 to 18 can also be synthesized by using a DNA synthesizer. According to the amino acid sequences represented by SEQ ID NOS:6 to 10, the primers for such oligonucleotides may be designed as primers in PCR for cloning a gene fragment encoding each protein, and can also be used as primers wherein all possible bases capable of encoding the amino acids are mixed. By PCR where these primers are used and a cDNA of fat body of Coconut rhinoceros beetle larvae immunized by inoculation with *E. coli* is used as the template, the DNA of the invention in any one of SEQ ID NOS: 1 to 5 can be amplified and isolated.

The recombinant vector of the present invention can be prepared by integrating a DNA fragment of the gene of the present invention into a suitable vector such as plasmid by methods described by for example Sambrook, J. et al. in Molecular cloning, A Laboratory Manual, second edition, Cold Spring Harbor Laboratory, 1.53 (1989), etc.

The vector can be prepared easily by ligating the desired gene in a usual manner to a recombinant vector (for example, plasmid DNA etc.) available in the art. Examples of the vector used include, but are not limited to, *Escherichia coli*-derived plasmids such as pBluescript, pUC18, pUC19, pBR322, etc.

For the purpose of producing the desired protein, the so-called expression vector is useful. The type of the expression vector is not particularly limited insofar as it has a function of expressing the desired gene in various host cells such as prokaryotic cells and/or eukaryotic cells thereby producing the desired protein, and preferable examples include *Escherichia coli* expression vectors such as pQE-30, pQE-60, pMAL-c2, pMAL-P2 and pSE420, yeast expression vectors such as pYES2 (for the genus *Saccharomyces*), pPIC3.5k, pPIC9k and pAO815 (all of which are for the genus *Pichia*), and insect expression vectors such as pBacPAK8/9, pBK283, pVL1392 and pBlueBac4.5.

When the protein of the present invention is produced by using yeasts, plant cells, animal cells or insect cells as host cells, it is preferable that generally the expression vector contains at least a promoter, an initiation codon, a gene encoding the desired antimicrobial protein, a termination codon and a terminator. Further, the expression vector may suitably contain a DNA encoding a peptide signal, an enhancer sequence, non-translating regions in the 5'- and 3'-terminal sides of the desired gene, a selective marker region or a unit of capable of replication.

The suitable initiation codon in the vector of the present invention is for example a methionine codon (ATG). Examples of the termination codon include ordinary termination codons (for example, TAG, TGA, TAA etc.).

The unit capable of replication refers to a DNA having an ability to replicate its whole DNA sequence in host cells, and includes natural plasmids, artificially modified plasmids (plasmids prepared from natural plasmids) and synthetic plasmids. Suitable plasmids include plasmid pQE30, pET, pCAL or artificially modified plasmids thereof (DNA fragments obtained by treating pQE30, pET or pCAL with a suitable restriction enzyme) for *E. coli*, plasmid pYES2 and pPIC9k for yeasts, and plasmid pBacPAK8/9 for insect cells.

The promoter used may be selected suitably depending on host and the purpose of expression and includes, but is not limited to, T7 promoter, lac promoter, trp promoter, λPL promoter etc. for *E. coli* as host, PHO5 promoter, GAP promoter, ADH promoter etc. as yeasts as host, SV40-derived promoter, retrovirus promoter etc. for animal cells as host. The enhancer sequence and terminator sequence used may be those used ordinarily by those skilled in the art, such as sequences derived from SV40.

As the selective marker, an ordinarily used one can be used in a usual manner. For example, a gene resistant to antibiotics such as tetracycline, ampicillin, kanamycin, neomycin, hygromycin or spectinomycin can be mentioned.

The expression vector can be prepared by ligating at least the above-mentioned promoter, initiation codon, gene encoding the desired antimicrobial protein, termination codon, and terminator region continuously and cyclically to the unit capable of replication. If necessary, a suitable DNA fragment (for example, a linker, other restriction sites etc.) can be used by conventional methods using digestion with a restriction enzyme and ligation with T4 DNA ligase.

The method of introducing the DNA into a vector is known (see J. Sambrook et al., Molecular Cloning, a Laboratory Manual, 2nd ed., Cold Spring Harbor Laboratory, New York, 1989). That is, the DNA and vector are digested respectively with a suitable restriction enzyme, and the resulting fragments may be ligated to each other with a DNA ligase.

The recombinant vector thus obtained, preferably a recombinant plasmid, can be introduced in a suitable host cell. The host cell used is not particularly limited insofar as it is compatible with the expression vector of the present invention and capable of being transformed therewith, and various cells such as natural cells usually used in the technical field of the present invention, or artificially established recombinant cells, can be used. The host cell is preferably an *E. coli*, yeast or insect cell, and specifically, the *E. coli* cell is M15, JM109, BL21 etc., the yeast cell is INVScl (genus *Saccharomyces*), GS115 and KM71 (both of which belong to the genus *Pichia*), and the insect cell is BmN4, silk worm larva etc. The animal cell includes cells derived from mice, *Xenopus*, rats, hamsters, monkeys or humans, or cultured cell strains established from these cells. The plant cell is not particularly limited insofar as the cell can be cultured, and examples thereof include cells derived from tobacco, *Arabidopsis*, rice, corn and wheat.

The transformant can be prepared by introducing the desired expression vector into a host cell. The method of introducing the DNA into a host cell includes a calcium chloride method, a calcium chloride/rubidium chloride method, an electroporation method, an electroinjection method, a method of chemical treatment with PEG etc., and a method of using a gene gun etc. described by Sambrook, J. et al. in Molecular Cloning, A Laboratory Manual, 2nd edition, Cold Spring Harbor Laboratory, 1.74 (1989).

Particularly, microorganisms (*E. coli, Bacillus subtilis* etc.) can be transformed by, for example, a method of Cohen et al. (Proc. Natl. Acad. Sci. USA, 1972; 69:2110), a protoplast method (Mol. Gen. Genet. 1979; 168:111) and a competent method (J. Mol. Biol. 1971; 56:209), *Saccharomyces cerevisiae* by for example a method of Hinnen et al. (Proc. Natl. Acad. Sci. USA. 1978; 75:1927) and a lithium method (J. Bacteriol. 1983; 153:163), plant cells by for example a leaf disk method (Science, 1985; 227:129) and an elecroporation method (Nature. 1986; 319:791), animal cells by for example a method of Graham (Virology. 1973; 52:456), and insect cells by for example a method of Summers et al. (Mol. Cell. Biol. 1983; 3:2156–2165).

(Transformed Plant)

The transformed plant of the present invention is a plant (or an offspring thereof) rendered resistant to plant-pathogenic microorganism etc., which is regenerated on the basis of host plant cells transformed with the gene of the present invention located under the control of a suitable promoter capable of functioning in plant cells, or with the gene of the present invention integrated in a suitable vector.

The transformed plant of the present invention can express, in its body, the protein having an antimicrobial activity according to the present invention.

The expression vector usable in the method of transforming plant cells with the gene of the present invention include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also be mentioned. The terminator gene to be ligated includes 35S terminator gene and Nos terminator gene.

The method of introducing the constructed expression vector into a plant includes an indirect introduction method and a direct introduction method. The indirect introduction includes, for example, a method using *Agrobacterium*. The direct introduction method includes, for example, an electroporation method, a particle gun method, a polyethylene glycol method, a microinjection method, a silicon carbide method etc.

The method of regenerating a plant individual from the transformed plant cells is not particularly limited, and may make use of techniques known in the art.

(Protein Having an Antimicrobial Activity)

The protein of the present invention can be produced by methods used conventionally for protein purification and isolation by a suitable combination of various kinds of column chromatography (C18, C8, gel filtration, ion-exchange) according to the Examples described later. The protein can be easily purified particularly by heat-treating hemolymph of Coconut rhinoceros beetle larvae at 100° C. for 10 minutes.

The protein of the present invention can be prepared in this manner from naturally expressing Coconut rhinoceros beetle, but the protein can also be prepared by a chemical synthesis method using a peptide synthesizer (for example, peptide synthesizer 430A manufactured by Perkin Elmer Japan) or by a recombination method using a suitable host cell selected from prokaryotes and eukaryotes. From the viewpoint of purity, a chemically synthesized protein or production by genetic engineering techniques and a recombinant protein are preferable.

Synthesis of a protein consisting of the amino acid sequence represented by any one of SEQ ID NOS: 6 to 10 by a conventional peptide synthesizer does not require any particular techniques and can be carried out under general synthesis conditions.

Further, an expression vector having any one of the DNA sequences in SEQ ID NOS: 1 to 5 and amplifiable in the desired hosts illustrated above is used to transform *E. coli*, yeasts, insects or animal cells, and the transformed cells are cultured under suitable culture conditions, whereby a large amount of the protein can be obtained as a recombinant.

Culture of the transformant can be carried out by general methods. For culture of the transformant, there are various literatures (see, for example, Microbial Experimental Methods (in Japanese) edited by the Japanese Biochemical Society and published by K. K. Tokyo Kagaku Dojin, 1992), and thus the transformant can be cultured by reference to such literature.

The method used in purifying the protein of the present invention from a culture mixture can be suitably selected from methods used usually in protein purification. That is, a proper method can be selected suitably from usually used methods such as salting-out, ultrafiltration, isoelectric precipitation, gel filtration, electrophoresis, ion-exchange chromatography, hydrophobic chromatography, various kinds of affinity chromatography such as antibody chromatography, chromatofocusing, adsorption chromatography and reverse phase chromatography, using a HPLC system etc. if necessary, and these techniques may be used in purification in a suitable order.

Further, the protein of the present invention can also be expressed as a fusion protein with another protein or a tag (for example, glutathione S transferase, protein A, hexahistidine tag, FLAG tag, etc.). The expressed fusion protein can be cleaved off with a suitable protease (for example, thrombin etc.), and preparation of the protein can be carried out more advantageously in some cases. Purification of the protein of the present invention may be carried out by using a suitable combination of general techniques familiar to those skilled in the art, and particularly upon expression of the protein in the form of a fusion protein, a purification method characteristic of the form is preferably adopted.

Further, a method of obtaining the protein by using the recombinant DNA molecule in a cell-free synthesis method (J. Sambrook, et al.: Molecular Cloning 2nd ed. (1989)) is one of the methods for producing the protein by genetic engineering techniques.

The protein of the present invention can be prepared as it is, or in the form of a fusion protein with another protein, but the protein of the present invention can be changed into various forms without limitation to the fusion protein. For example, the processing of the protein by various techniques known to those skilled in the art, such as various chemical modifications of the protein, binding thereof to a polymer such as polyethylene glycol, and binding thereof to an insoluble carrier, may be conducted. The presence or absence of addition of sugar chains or a difference in the degree of addition of sugar chains can be recognized depending on the host used. The proteins in such cases are also construed to be under the concept of the present invention insofar as they function as proteins having an antimicrobial activity.

(Fungicide, Antimicrobial Agent, and Industrial Antimicrobial/Antifungal Agent)

The antimicrobial agent, fungicide or industrial antimicrobial/antifungal agent of the present invention can be prepared from the protein of the present invention alone or by mixing the protein with a solution, a suspension or an emulsion if necessary. In the aqueous or non-aqueous solution or suspension, at least one active substance is mixed with at least one inert diluent. The aqueous diluent includes, for example, distilled water, saline, etc. The non-aqueous diluent includes, for example, propylene glycol, polyethylene glycol, vegetable oils such as olive oil, and alcohols such as ethanol.

Such compositions may further include additives such as a preservative, a wetting agent, an emulsifying agent, a dispersant or a stabilizer (for example, arginine, aspartic acid etc.). These additives are sterilized if necessary by filtration through a bacteria-retention filter or by compounding with another fungicide or by irradiation. These additives can be produced in the form of a sterile solid composition by e.g. lyophilization and used after dissolving it in pyrogen-free distilled water or other solvents.

The form of the antimicrobial agent, fungicide or industrial antimicrobial/antifungal agent thus obtained maybe determined depending on intended use, mixed with the above-mentioned additives and sprinkled in the form of tablets, pills, powder, granules, liquids, emulsions etc.

The agricultural and horticultural fungicides etc. comprising the protein of the invention having an antimicrobial activity as the active ingredient can be utilized in prevention and treatment of plant diseases in which fungi or microorganisms are involved. Usually, the fungicide etc. of the present invention can be sprinkled generally or topically onto a plant.

The amount of the protein having an antimicrobial activity applied as an agent for controlling plant diseases is varied depending on application site, application time, application method, cultivated crops etc., but generally the amount of the protein as the active ingredient is about 0.001 to 10 kg/ha, preferably about 0.001 to 5 kg/ha. The fungicide etc. can be sprinkled once to several times per day, depending on the type of plant, growth stage, symptoms, application method, treatment time, the type of protein sprinkled (the full-length protein, a protein with partial substitution, deletion, insertion and/or addition in the full-length protein, etc.), climate in a place for growth, soil in a place for growth, etc.

The antimicrobial agent etc. for pharmaceutical preparations according to the present invention can be prepared from the protein of the present invention alone or by compounding the protein with pharmaceutically acceptable excipients, active ingredients, fillers etc. if necessary. The preparation form includes parenteral administration forms such as injections (subcutaneous, intravenous, intramuscular or intraperitoneal injections), liquid coating agents, gel, ointments, suppositories and aerosol, and oral administration forms such as tablets, capsules, granules, pills, syrups, liquids, emulsions, suspensions etc.

For preparation of the tablets, capsules, granules and pills for oral administration, use is made of excipients such as white sugar, lactose, glucose, starch and mannitol, binders such as syrup, gum arabic, gelatin, sorbitol, tragacanth, methylcellulose and polyvinyl pyrrolidone, disintegrating agents such as starch, carboxymethyl cellulose or a calcium salt thereof, fine crystalline cellulose and polyethylene glycol, lustering agents such as talc, magnesium stearate, calcium stearate and silica, and lubricants such as sodium laurate and glycerol.

For preparation of the injections, liquids, emulsions, suspensions, syrups and aerosol, use is made of solvents for the active ingredient, such as water, ethyl alcohol, isopropyl alcohol, propylene glycol, 1,3-butylene glycol and polyethylene glycol, surfactants such as sorbitan fatty ester, polyoxyethylene sorbitan fatty ester, polyoxyethylene fatty ester, hydrogenated castor oil polyoxyethylene ether, and lecithin, cellulose derivatives such as carboxymethylcellulose sodium salt and methylcellulose, suspending agents such as natural gum such as tragacanth and gum arabic, preservatives such as paraoxybenzoate, benzalkonium chloride and sorbitate.

For preparation of the ointments as subcutaneously absorbed preparations, for example white Vaseline, liquid paraffin, higher alcohols, macrogol, an aqueous gelling base etc. are used. For preparation of the suppositories, for example polyethylene glycol, lanolin, coconut oil etc. are used.

The pharmaceutical composition containing the protein of the present invention having an antimicrobial activity contains this protein in an amount of about 0.1 to 99.5%, preferably about 0.5 to 95%, based on the weight of the entire composition. In addition to this protein or the composition containing this protein, other pharmaceutically active compounds can be contained, and a plurality of the proteins of the present invention may be contained.

The clinical dose of this protein is varied depending on the age, body weight, sensitivity and symptom of the patient, but usually the effective daily dose is 0.003 to 1.5 g, preferably 0.01 to 0.6 g per man. However, a dose outside of the above range can also be used if necessary.

When the industrial antimicrobial/antifungal agent of the present invention is prepared, there is no upper limit to the concentration of this protein as the active ingredient insofar as the liquids, hydrates, emulsions, sol and other suitable preparations can be prepared, but this protein is compounded in a ratio of 1 to 90 weight %, preferably 3 to 40 weight %, based on the weight of such preparations.

The usable carrier may be any solid or liquid carrier which is customarily used in industrial antimicrobial/antifungal agents, and is not limited to any specific carrier. Examples of the solid carrier include mineral powder of kaolin, bentonite, clay, mommolinite etc. Examples of the liquid carrier include water, alcohols such as methyl alcohol, ethyl alcohol and nitriles such as acetonitrile, propionitrile etc.

In addition, thickening agents such as polyvinyl alcohol (PVA), carboxymethylcellulose (CMC), gum arabic, xanthene gum, hydroxypropyl cellulose etc. and various auxiliary agents can be incorporated. Further, a stabilizer such as UV absorber can be added if necessary in a suitable amount.

Hereinafter, the resent invention is described in more detail by reference to the Examples, but the present invention is not limited by the Examples.

EXAMPLES

Example 1

Purification of a Protein Having an Antimicrobial Activity

1) Collection of a Hemolymph of Coconut Rhinoceros Beetle Larvae

Three-week-old Coconut rhinoceros beetle larvae were inoculated with $E.$ $coli$ (JM109, $10^6$ cells/larva) to induce a protein having an antimicrobial activity, and 15 hours later, their hemolymph was collected in physiological saline containing a protease inhibitor dissolved therein. The resulting hemolymph was heat-treated at 100° C. for 10 minutes, followed by removing insolubles by centrifugation, to give a heat-treated hemolymph.

2) Purification of the Antimicrobial Protein by Column Chromatography

Isolation of the antimicrobial protein was conducted by using a method of evaluating an anti-filamentous fungal activity as described later.

The heat-treated hemolymph was passed through Sep-pak Vac C18 (Waters) equilibrated with 0.05% trifluoroacetic acid (TFA) to adsorb the antimicrobial protein. After the Sep-pak column was washed with 0.05% TFA, the antimicrobial protein was eluted with 20, 40 and 60% acetonitrile (0.05% TFA). Each eluted fraction was concentrated in a centrifugal evaporator to remove the acetonitrile, and then evaluated for its anti-filamentous fungal activity. The 40% elution fraction exhibiting the highest activity was applied onto a 1 ml Resourse RPC column (Pharmacia) connected to AKTA (Pharmacia), and then the antimicrobial protein was eluted with a gradient of 20 to 40% acetonitrile (0.05% TFA) at a flow rate of 1 ml/min. Under these conditions, active fractions eluted with 26 to 32% were recovered and concentrated in a centrifugal evaporator. The active fractions thus obtained were applied onto Senshupak VP-318 Φ4.6×

250 mm (Senshu) connected to Waters HPLC (600E System controller, 486 Tunable Absorbance Detector, 626 Pump), and the antimicrobial protein was eluted with a gradient of 20 to 26% acetonitrile (0.05% TFA) at a flow rate of 1 ml/min.

Figure 1:
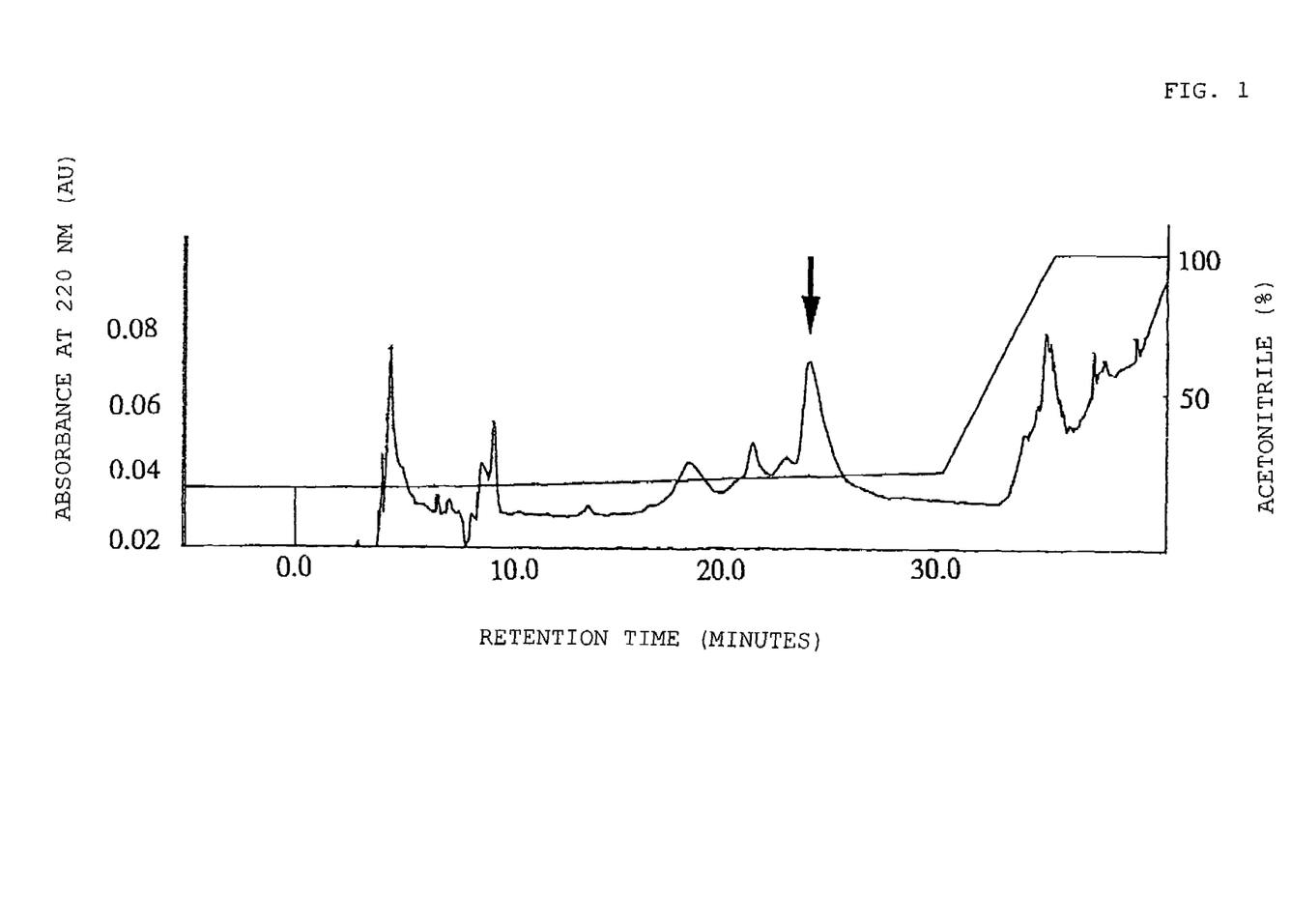
FIG. 1 shows a chart in final purification of an antimicrobial protein from hemolymph of Coconut rhinoceros beetle larvae.
Figure 2:
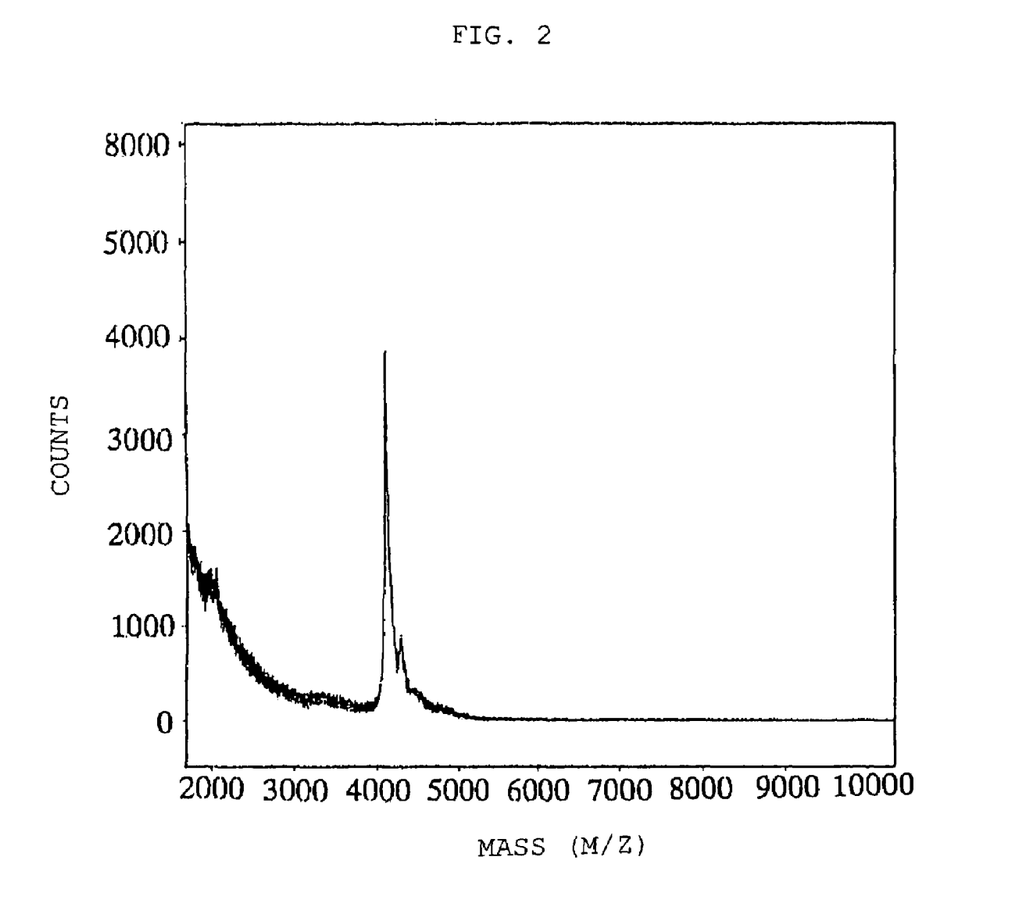
FIG. 2 shows MALDI-TOF MS analysis of an antimicrobial protein purified from hemolymph of Coconut rhinoceros beetle larvae.

Each peak was collected under monitoring absorbance at 220 nm and evaluated for its anti-filamentous fungal activity. An active peak eluted with 22 to 23% acetonitrile was applied onto Senshupak VP-318 Φ4.6×250 mm (Senshu) connected to Waters HPLC, and the antimicrobial protein was eluted with a gradient of 30 to 40% acetonitrile [0.05% heptafluorobutanoic acid (HFBA)] at a flow rate of 1 ml/min. Each peak was collected under monitoring absorbance at 220 nm and evaluated for its anti-filamentous fungal activity. An active peak eluted with 24 to 27% acetonitrile was applied onto a Sephasil C8 SC 2.1/10 column (Pharmacia) connected to SMART (Pharmacia) and eluted with a gradient of 20 to 26% acetonitrile (0.05% TFA) at a flow rate of 0.1 ml/min. Each peak was collected under monitoring absorbance at 220 nm and evaluated for its anti-filamentous fungal activity (FIG. 1). The peak confirmed to have an activity was analyzed by matrix-assisted laser desorption ionization time-of-flight mass spectrometry (MALDI-TOF MS, Voyager BioSpectrometry Workstation, Perseptive Biosystems) The resulting fraction contained a component having a molecular weight of 4080 Da as a main peak (first component) and also contained a component having a molecular weight of 4266 Da (second component) (FIG. 2). Purification of these components was attempted by using various columns, but it was difficult to separate these components from each other.

3) System for Evaluation of Anti-Filamentous Fungal Activity

*Rhizoctonia solani* microorganisms were cultured in a potato dextrose (PD) medium (Difco) at 25° C. for 5 days, and then their hyphae were cut thin with a homogenizer. From the resulting suspension of thin hyphae, a clump of hyphae was removed, and the hyphae were recovered by centrifugation and adjusted to a density of $10^5$ hyphae/ml with PD medium. A PDA medium was added in a solution form to 250 µl hypha suspension to form 5 ml suspension which was then spread on a Petri dish (diameter, 8.4 cm). After the medium was solidified, 1 µl sample for activity evaluation was spotted thereon followed by culture for 24 hours at 25° C., and the size of an inhibitory circle formed around the spot was measured.

Example 2

Isolation of cDNA for an Antimicrobial Peptide

1) Amino Acid Analysis of the Antimicrobial Protein

The active fraction containing both the first and second components in 2) in Example 1 was analyzed for N-terminal amino acid sequence by Edman degradation in a protein sequencer (492cLC Protein Sequencer, PE Applied Biosystems). As a result, the N-terminal sequence of the first component was ELPKLPDDKVLIRSRSNXPK, and the N-terminal sequence of the second component was DAELPKLPDD. From the difference in molecular weight and the amino acid sequence of 10 residues from the N-terminal, it was estimated that the second component was a protein having 2 amino acid residues added to the first component.

For further analysis of the amino acid sequence, the antimicrobial protein was partially digested with endoprotease Arg-C (Boehringer Mannheim) to analyze the amino acid sequence. As a result, the amino acids after the 21st residue was GKVWDGF, and the amino acid sequence of from the N-terminal to the 27th residue could be determined.

2) Design of Degenerate Primers for 3'-RACE

On the basis of the amino acid sequence determined above, the following 3 primers having all possible bases mixed therein were synthesized (Tm of 50 to 55° C.): P4080-1 (5'-aarytnccngaygayaargt-3') (SEQ ID NO:12), P4080-2 (5'-ccngaygayaargtnytnat-3') (SEQ ID NO:13), P4080-3 (5'-gaygcngarytnccnaa-3') (SEQ ID NO:14) wherein r represents a or g, y represents c or t, and n represents a, t, c or d.

3) Synthesis of cDNA from Fat Body of Coconut Rhinoceros Beetle Larvae

From a fat body of 3-week-old Coconut rhinoceros beetle larvae six hours after inoculation with *E. coli*, mRNA was extracted by ISOGEN (Nippon Gene), and 3 µg of the mRNA was used to synthesize cDNA by using a first-strand cDNA synthetic kit (Amershampharmacia). All procedures were in accordance with a protocol attached to the kit.

4) 3'-RACE

The 3'-region of the antimicrobial protein was screened by PCR using the primers synthesized above and the cDNA synthesized as a template in 2) by using NotI-dt primers attached to the kit. The amplified fragment was purified on gel and cloned with a TA cloning kit (Invitrogen). The DNA sequence of the amplified fragment was determined by a DNA sequencer (377 DNA Sequencer, PE Applied Biosystems). A amplification fragment whose coding amino acid sequence, deduced from its DNA sequence, agreed with the sequence obtained by the protein sequencer was obtained, and the DNA sequence of the 3'-region of the antimicrobial protein was determined.

5) Design of Degenerate Primers for 5'-RACE

On the basis of the DNA sequence determined by 3'-RACE, the following 3 primers for 5'-RACE were synthesized (Tm of 50 to 65° C.): P4080-4 (5'-cgatatacaagcatcaatgc-3') (SEQ ID NO:15), P4080-5 (5'-gcgaacggtgatttacagtcaaatccattc-3') (SEQ ID NO:16) and P4080-6 (5'-gccttttggacagttactcctacttctaat-3') (SEQ ID NO:17).

6) 5'-RACE

Using the above synthetic primers, the mRNA recovered from the fat body described above was used to synthesize 5' region cDNA with 5'-RACE System for Rapid Amplification of cDNA End Reagent Assembly (GIBCO BRL).

Two primers, and universal amplification primers attached to the kit, were used in screening the 5'-region cDNA synthesized above. The amplified fragment was cloned to determine the DNA sequence. A amplification fragment whose coding amino acid sequence, deduced from its DNA sequence, agreed with the sequence obtained by the protein sequencer was obtained, and the DNA sequence of the 5'-region of the antimicrobial protein was determined.

7) Acquisition of Full-Length cDNA

On the basis of the upstream sequence obtained by 5'-RACE, a primer was synthesized (P4080-7, 5'-aagggacgatcaaaatgaaa-3') (SEQ ID NO:18) and used together with the NotI-dt primers, to screen the cDNA synthesized above. The amplified fragment was cloned to determine the DNA sequence. A full-length cDNA completely agreeing with the DNA sequences obtained by 3'- and 5'-RACE was obtained. As a result, the cDNA encoding the antimicrobial protein of the invention derived from a hemolymph of Coconut rhinoceros beetle larvae was composed of 201 bases in total encoding 66 amino acids. By searching for homology (BLAST) of the amino acid sequence and DNA sequence with those in a data base (SWISS PROT), there was no sequence having high homology therewith, and thus the present protein was considered to be a novel protein.

The amino acid 18 which was the only amino acid not determined in the 4080 Da sequence was revealed to be cysteine (Cys), from the cDNA sequence corresponding to this position. Cysteine cannot be analyzed by Edman degradation and could thus not be detected by amino acid sequencing.

Because there was a difference in molecular weight by 258 Da between the protein deduced from the full-length cDNA and the protein obtained from the hemolymph of Coconut rhinoceros beetle larvae, analysis of the C-terminal of the natural protein was conducted using Sequazyme C-peptide Sequence kit (Perseptive Biosystems) and MALDI-TOF MS. As a result, the antimicrobial protein obtained by purification from the hemolymph of Coconut rhinoceros beetle larvae was estimated to have serine (Ser), phenylalanine (Phe) and alanine (Ala) from the C-terminal, thus revealing that C-terminal two lysine (Lys) residues were cut off from the mature protein deduced from the cDNA.

Example 3

Evaluation of the Activity of Synthetic Protein

1) Synthesis of Protein

Four kinds of proteins (SP4080, SP4266, SP4337, SP4523) which on the basis of the amino acid sequence deduced from the cDNA, were considered as mature proteins were synthesized by the F-mok method by using an automatic protein synthesizer (9050 Plus Pepsynthesizer, Perseptive Biosystems).

2) Formation of Disulfide Linkages

After about 30 mg protein obtained by the synthesis was dissolved in 90 ml of 10 mM Tris-HCl (pH 8.0), 5 ml of 5 mM 2,2'-bispyridyl disulfide was added thereto and the mixture was stirred at room temperature for 10 minutes to form disulfide linkages.

3) Purification of the Synthetic Protein

The solution of the protein having formed disulfide linkages was applied onto a μBondasphere Φ20×150 mm (Waters) column connected to AKTA, and then eluted with a gradient of 25 to 32% acetonitrile (0.05% TFA) at a flow rate of 12 ml/min. Each peak was collected under monitoring absorbance at 220 nm and analyzed by MALDI TOF MS. The acetonitrile was removed by a centrifugal evaporator from a fraction containing a peak showing the objective molecular weight, and the sample was applied onto a μBondasphere Φ20×150 mm (Waters) column connected to AKTA, and then eluted with a gradient of 35 to 40% acetonitrile (0.05% HFBA) at a flow rate of 12 ml/min. Each peak was collected under monitoring absorbance at 220 nm and analyzed by MALDI TOF MS, and a fraction containing a peak showing the objective molecular weight was recovered. The resulting fraction was analyzed with a gradient of 20 to 30% acetonitrile by a PEGASIL ODS Φ4.6×250 mm column (Senshu) connected to Agilent 1100 Series (Hewlett Packard), and confirmed to have 90% or more purity. The amino acid sequence of the resulting synthetic protein was confirmed by a protein sequencer, and the synthetic protein was confirmed to be the same as the protein deduced from the cDNA.

4) Evaluation of the Antimicrobial Activity of the Synthetic Protein

The above-described method of evaluating anti-*Rhizoctonia solani* activity was used to evaluate the activity of the 4 synthetic proteins. As a result, any proteins exhibited almost the same activity (Table 1).

TABLE 1

Anti-*Rhizoctonia solani* activity of the synthetic peptides

| | Inhibitory circle | | | |
|---|---|---|---|---|
| | SP4080 | SP4266 | SP4337 | SP4523 |
| *Rhizoctonia solani* | ◎ | ◎ | ◎ | ◎ |

◎; Inhibitory circle of 4 mm or more
○; Inhibitory circle of less than 4 mm
X; No activity To examine the activity spectrum of the antimicrobial proteins, microbial strains such as *Pyricularia oryzae, Septoria tritici, Rhizoctonia solani* Kuhn, *Phytophthora infestance, Staphylococcus aureus* and *Escherichia coli* were used to evaluate the activity.

*Pyricularia oryzae, Septoria tritici* and *Rhizoctonia solani* Kuhn were evaluated for the antimicrobial activity in the same manner as for *Rhizoctonia solani*. *Phytophthora infestance* was cultured at 20° C. in V8 juice medium. *Staphylococcus aureus* and *Escherichia coli* were cultured at 37° C. for 12 hours in a nutrient broth (NB) medium (Difco) until the absorbance at 596 nm reached 0.01, and an NBA medium containing 500 μl of the microbial suspension was added in an amount of 5 ml and spread in a Petri dish (diameter 8.4 cm) and used as a plate for activity evaluation. 50 μg antimicrobial protein was spotted for each strain, and a growth inhibitory circle formed therearound was measured (Table 2).

TABLE 2

Antimicrobial activity of SP4080

| Bacterial strain | Inhibitory circle |
|---|---|
| *Pyricularia oryzae* | ○ |
| *Rhizoctonia solani* Kuhn | ◎ |
| *Septoria tritici* | ○ |
| *Phytophthora infestance* | ○ |
| *Staphylococcus aureus* | ◎ |
| *Escherichia coli* | ◎ |

◎; Inhibitory circle of 4 mm or more
○; Inhibitory circle of less than 4 mm
X; No activity The present antimicrobial protein exhibited a strong activity to form a growth inhibitory circle of 4 mm or more on *Rhizoctonia solani, Rhizoctonia solani* Kuhn, *Staphylococcus aureus* and *Escherichia coli*, and also exhibited a strong activity on *Pyricularia oryzae, Septoria tritici* and *Phytophthora infestance*.

From the foregoing, it was demonstrated that the antimicrobial proteins of the present invention derived from the hemolymph of Coconut rhinoceros beetle larvae have an antimicrobial activity on various plant-pathogenic filamentous fungi and pathogenic microorganism.

INDUSTRIAL APPLICABILITY

A pharmaceutical preparation comprising the protein of the present invention as the active ingredient can be expected to be usable as an agricultural and horticultural fungicides or an antimicrobial agent for pharmaceutical preparations, which is strong and has a broad spectrum.

The invention claimed is:

1. An isolated protein comprising an amino acid sequence represented by any one of SEQ ID NOS: 6 to 10.

2. A fungicide, an antimicrobial agent or an industrial antimicrobial/antifungal agent comprising as an active ingredient any one of the proteins described in claim 1.

3. The fungicide, antimicrobial agent or industrial antimicrobial/antifungal agent according to claim 2, which is used in agriculture and horticulture, in pharmaceutical preparations or in industry.

* * * * *

SEQUENCE LISTING

<160> NUMBER OF SEQ ID NOS: 18

<210> SEQ ID NO 1
<211> LENGTH: 201
<212> TYPE: DNA
<213> ORGANISM: Oryctes rhinoceros

<400> SEQUENCE: 1

```
atgaaaacgt taacgtttta tactctatta ctatgtgctg ctctttatag taatttcttc      60
gattgtaaag ccgttgcgga tgcggaattg ccgaaattac cagatgacaa agttttgatt    120
agaagtagga gtaactgtcc aaaaggcaaa gtatggaatg gatttgactg taaatcaccg    180
ttcgcattta gcaaaaagtg a                                              201
```

<210> SEQ ID NO 2
<211> LENGTH: 108
<212> TYPE: DNA
<213> ORGANISM: Oryctes rhinoceros

<400> SEQUENCE: 2

```
gaattgccga aattaccaga tgacaaagtt ttgattagaa gtaggagtaa ctgtccaaaa      60
ggcaaagtat ggaatggatt tgactgtaaa tcaccgttcg catttagc                 108
```

<210> SEQ ID NO 3
<211> LENGTH: 114
<212> TYPE: DNA
<213> ORGANISM: Oryctes rhinoceros

<400> SEQUENCE: 3

```
gatgcggaat tgccgaaatt accagatgac aaagttttga ttagaagtag gagtaactgt      60
ccaaaaggca agtatggaa tggatttgac tgtaaatcac cgttcgcatt tagc            114
```

<210> SEQ ID NO 4
<211> LENGTH: 114
<212> TYPE: DNA
<213> ORGANISM: Oryctes rhinoceros

<400> SEQUENCE: 4

```
gaattgccga aattaccaga tgacaaagtt ttgattagaa gtaggagtaa ctgtccaaaa      60
ggcaaagtat ggaatggatt tgactgtaaa tcaccgttcg catttagcaa aaag           114
```

<210> SEQ ID NO 5
<211> LENGTH: 120
<212> TYPE: DNA
<213> ORGANISM: Oryctes rhinoceros

<400> SEQUENCE: 5

```
gatgcggaat tgccgaaatt accagatgac aaagttttga ttagaagtag gagtaactgt      60
ccaaaaggca agtatggaa tggatttgac tgtaaatcac cgttcgcatt tagcaaaaag    120
```

<210> SEQ ID NO 6
<211> LENGTH: 66
<212> TYPE: PRT
<213> ORGANISM: Oryctes rhinoceros

<400> SEQUENCE: 6

```
Met Lys Thr Leu Thr Phe Tyr Thr Leu Leu Leu Cys Ala Ala Leu Tyr
 1               5                  10                  15
```

```
Ser Asn Phe Phe Asp Cys Lys Ala Val Ala Asp Ala Glu Leu Pro Lys
            20                  25                  30

Leu Pro Asp Asp Lys Val Leu Ile Arg Ser Arg Ser Asn Cys Pro Lys
            35                  40                  45

Gly Lys Val Trp Asn Gly Phe Asp Cys Lys Ser Pro Phe Ala Phe Ser
 50                  55                  60

Lys Lys
 65

<210> SEQ ID NO 7
<211> LENGTH: 36
<212> TYPE: PRT
<213> ORGANISM: Oryctes rhinoceros

<400> SEQUENCE: 7

Glu Leu Pro Lys Leu Pro Asp Asp Lys Val Leu Ile Arg Ser Arg Ser
 1               5                  10                  15

Asn Cys Pro Lys Gly Lys Val Trp Asn Gly Phe Asp Cys Lys Ser Pro
            20                  25                  30

Phe Ala Phe Ser
        35

<210> SEQ ID NO 8
<211> LENGTH: 38
<212> TYPE: PRT
<213> ORGANISM: Oryctes rhinoceros

<400> SEQUENCE: 8

Asp Ala Glu Leu Pro Lys Leu Pro Asp Asp Lys Val Leu Ile Arg Ser
 1               5                  10                  15

Arg Ser Asn Cys Pro Lys Gly Lys Val Trp Asn Gly Phe Asp Cys Lys
            20                  25                  30

Ser Pro Phe Ala Phe Ser
        35

<210> SEQ ID NO 9
<211> LENGTH: 38
<212> TYPE: PRT
<213> ORGANISM: Oryctes rhinoceros

<400> SEQUENCE: 9

Glu Leu Pro Lys Leu Pro Asp Asp Lys Val Leu Ile Arg Ser Arg Ser
 1               5                  10                  15

Asn Cys Pro Lys Gly Lys Val Trp Asn Gly Phe Asp Cys Lys Ser Pro
            20                  25                  30

Phe Ala Phe Ser Lys Lys
        35

<210> SEQ ID NO 10
<211> LENGTH: 40
<212> TYPE: PRT
<213> ORGANISM: Oryctes rhinoceros

<400> SEQUENCE: 10

Asp Ala Glu Leu Pro Lys Leu Pro Asp Asp Lys Val Leu Ile Arg Ser
 1               5                  10                  15

Arg Ser Asn Cys Pro Lys Gly Lys Val Trp Asn Gly Phe Asp Cys Lys
            20                  25                  30

Ser Pro Phe Ala Phe Ser Lys Lys
        35                  40
```

<210> SEQ ID NO 11
<211> LENGTH: 310
<212> TYPE: DNA
<213> ORGANISM: Oryctes rhinoceros

<400> SEQUENCE: 11

```
aagggacgat caaatgaaa acgttaacgt tttatactct attactatgt gctgctcttt      60
atagtaattt cttcgattgt aaagccgttg cggatgcgga attgccgaaa ttaccagatg     120
acaaagtttt gattagaagt aggagtaact gtccaaaagg caaagtatgg aatggatttg    180
actgtaaatc accgttcgca tttagcaaaa agtgaagaat ttttagcatt gatgcttgta    240
tatcgtatat gtagtacgta tataggacga agctaataaa tattatgtaa tttctaaaaa    300
aaaaaaaaaa                                                            310
```

<210> SEQ ID NO 12
<211> LENGTH: 20
<212> TYPE: DNA
<213> ORGANISM: Artificial
<220> FEATURE:
<223> OTHER INFORMATION: primer P4080-1
<220> FEATURE:
<221> NAME/KEY: misc_feature
<222> LOCATION: (6)..(6)
<223> OTHER INFORMATION: n can be a, t, c, or g
<220> FEATURE:
<221> NAME/KEY: misc_feature
<222> LOCATION: (9)..(9)
<223> OTHER INFORMATION: n can be a, t, c, or g

<400> SEQUENCE: 12

```
aarytnccng aygayaargt                                                  20
```

<210> SEQ ID NO 13
<211> LENGTH: 20
<212> TYPE: DNA
<213> ORGANISM: Artificial
<220> FEATURE:
<223> OTHER INFORMATION: primer P4080-2
<220> FEATURE:
<221> NAME/KEY: misc_feature
<222> LOCATION: (3)..(3)
<223> OTHER INFORMATION: n can be a, t, c, or g
<220> FEATURE:
<221> NAME/KEY: misc_feature
<222> LOCATION: (15)..(15)
<223> OTHER INFORMATION: n can be a, t, c, or g
<220> FEATURE:
<221> NAME/KEY: misc_feature
<222> LOCATION: (18)..(18)
<223> OTHER INFORMATION: n can be a, t, c, or g

<400> SEQUENCE: 13

```
ccngaygaya argtnytnat                                                  20
```

<210> SEQ ID NO 14
<211> LENGTH: 17
<212> TYPE: DNA
<213> ORGANISM: Artificial
<220> FEATURE:
<223> OTHER INFORMATION: primer P4080-3
<220> FEATURE:
<221> NAME/KEY: misc_feature
<222> LOCATION: (6)..(6)
<223> OTHER INFORMATION: n can be a, t, c, or g
<220> FEATURE:
<221> NAME/KEY: misc_feature
<222> LOCATION: (12)..(12)

```
<223> OTHER INFORMATION: n can be a, t, c, or g
<220> FEATURE:
<221> NAME/KEY: misc_feature
<222> LOCATION: (15)..(15)
<223> OTHER INFORMATION: n can be a, t, c, or g

<400> SEQUENCE: 14
gaygcngary tnccnaa                                                    17

<210> SEQ ID NO 15
<211> LENGTH: 20
<212> TYPE: DNA
<213> ORGANISM: Artificial
<220> FEATURE:
<223> OTHER INFORMATION: primer P4080-4

<400> SEQUENCE: 15
cgatatacaa gcatcaatgc                                                 20

<210> SEQ ID NO 16
<211> LENGTH: 30
<212> TYPE: DNA
<213> ORGANISM: Artificial
<220> FEATURE:
<223> OTHER INFORMATION: primer P4080-5

<400> SEQUENCE: 16
gcgaacggtg atttacagtc aaatccattc                                      30

<210> SEQ ID NO 17
<211> LENGTH: 30
<212> TYPE: DNA
<213> ORGANISM: Artificial
<220> FEATURE:
<223> OTHER INFORMATION: primer P4080-6

<400> SEQUENCE: 17 gcctttgga cagttactcc tacttctaat                                       30

<210> SEQ ID NO 18
<211> LENGTH: 20
<212> TYPE: DNA
<213> ORGANISM: Artificial
<220> FEATURE:
<223> OTHER INFORMATION: primer P4080-7

<400> SEQUENCE: 18
aagggacgat caaaatgaaa                                                 20
```